United States Patent [19]

Palomo-Coll et al.

[11] Patent Number: 4,749,790

[45] Date of Patent: Jun. 7, 1988

[54] PROCESS FOR PREPARING $H_2$ RECEPTOR ANTAGONIST ASCORBATE COMPOUNDS

[75] Inventors: Antonio L. Palomo-Coll; Montserrat Ballester-Rodés, both of Barcelona; Francisco E. Polamo-Nicolau, Sant Cugat Del Valles, all of Spain

[73] Assignee: Barisintex, S.A, Spain

[21] Appl. No.: 875,615

[22] Filed: Jun. 18, 1986

[30] Foreign Application Priority Data

Jun. 28, 1985 [ES] Spain .................................. 544661
Jan. 7, 1986 [ES] Spain .................................. 550690

[51] Int. Cl.$^4$ .................. C07D 239/22; C07D 401/10; C07D 233/66; C07D 307/62
[52] U.S. Cl. .................. 544/320; 546/209; 548/183; 548/337; 549/315
[58] Field of Search .............. 548/337, 183; 549/315; 546/209; 544/320

[56] References Cited

U.S. PATENT DOCUMENTS 4,251,449  2/1981  Schreur .......................... 260/343.7

FOREIGN PATENT DOCUMENTS 1498600   9/1967  France .......................... 546/277
1510505  12/1967  France .......................... 546/277

58-103312  6/1983  Japan .......................... 546/277

Primary Examiner—John M. Ford
Assistant Examiner—J. Richter
Attorney, Agent, or Firm—Scully, Scott, Murphy & Presser

[57] ABSTRACT

$H_2$-receptor antagonist ascorbate compounds, derived from the lactone form of 3-ketohexuronic acid of Formula

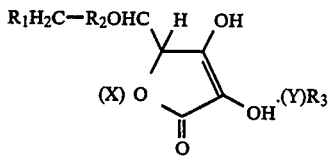

where (X) may be 1, 2 or 3 and (Y) may be 1 or 2, $R_1$ and $R_2$ are both hydrogen or $R_1$ may be hydroxyl, $R_2$ hydrogen or the O-alkylidene, 5,6-diacyl, 6-acyl derivatives thereof having two to sixteen carbon atoms, or a 6-phosphate, $R_3$ being an organic base or a salt thereof having one or more basic functional groups, having $H_2$-receptor antagonist properties and capable of reacting with nitrous acid, and a process for the preparation of said compounds.

10 Claims, 3 Drawing Sheets

PROCESS FOR PREPARING H₂ RECEPTOR ANTAGONIST ASCORBATE COMPOUNDS

BACKGROUND OF THE INVENTION

This invention relates to $H_2$-receptor antagonist ascorbates derived from the lactone form of 3-ketohexuronic acid of Formula I:

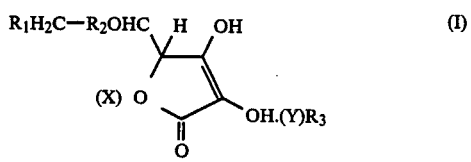

where (X) may be 1, 2 or 3 and (Y) may be 1 or 2, $R_1$ and $R_2$ are both hydrogen or $R_1$ may be hydroxyl, $R_2$ hydrogen or the O-alkylidene, 5,6-diacyl, 6-acyl derivatives thereof having two to sixteen carbon atoms, or a 6-phosphate, $R_3$ being an organic base or a salt thereof having one or more basic functional groups, having $H_2$-receptor antagonist properties and capable of reacting with nitrous acid.

The invention also relates to a process for the preparation of the above described compounds.

In the process a 3-ketohexuronic acid, or derivatives thereof, of the Formula II:

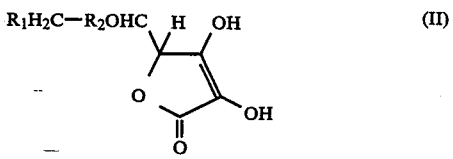

where $R_1$ and $R_2$ are as hereinbefore defined, is reacted at a temperature from 0° C. to 60° C. with an organic base or a salt thereof represented by $R_3$ as hereinbefore defined, to give a compound of Formula I.

DESCRIPTION OF THE PRIOR ART

The $H_2$-receptor antagonist ascorbates are compounds of interest in human medicine and veterinary science for combatting disorders of the oesophagus, stomach and duodenum, such as peptic oesophagitis, treatment of oesophagic and gastric hemorrhages such as hypersecretion, gastric ulcer, duodenal ulcer and the Zollinger-Ellison syndrome. The structure of the new compounds comprises cimetidine, ranitidine and famotidine, among others, described in Drugs of the Future, Vol. 8, No. 2 (1983), the ascorbates of which are effective anti-ulcer agents. They may be applied medicinally in any of the forms known and used in Galenic art, such as tablets, pills, capsules, microcapsules, injections, extemporaneous forms, etc.

Very many N-nitroso derivatives of amines and amides are carcinogenic to man and animals, as discussed in "Safety Evaluation of Nitrosatable Drugs and Chemicals, Ed. G. G. Gibson and C. Ioannides; Taylor-Francis Ltd. 1981" and references are made hereinafter thereto, with an indication of the page in brackets. Schmahl (8), starting out from a fairly conservative estimate of the intragastric formation of N-nitroso compounds, came to the conclusion that the dose-response studies for evaluation of the human risk provide no absolute proof of susceptibility, but indicate that the situation in man may be comparable to that observed in experimental animals.

According to Walker (220 to 228), the extent to which dietary precursors are converted into N-nitroso compounds, nitrosamines synthetised "in vivo", probably exceeds that from preformed dietary nitrosamines. The high risk groups would be those having a high nitrite and nitrate level, with high pH, which would allow bacterial colonisation of the stomach. The formation of nitrosamines was shown by incubating food homogenates with gastric juice or simulated gastric juice. Tannenbaum (234 to 241) states that the risk of gastric cancer increases with an increase of nitrite in the diet as precursor of the nitrosation of organic bases, an elevation of pH and the presence of bacteria in excess (conversion of nitrates into nitrites), all associated with chronic gastritis. The nitrosation may be maximised with acid and alkaline pH cycles in the stomach. In the latter state there is an accumulation of nitrites (hypochlorhydria or achlorhydria), while under acidic conditions (hyperchlorhydria), there is an increase in the rate of nitrosation. For the same reason, an equally serious situation could exist if the stomach were to become regionally alkaline and acidic at the same time.

Therefore, the above cited author suggested that the gastric nitrosation could be blocked by compounds competing for the nitrite, such as ascorbic acid, which should be considered for intervention in potential risk situations. To prevent the formation of a toxic N-nitroso compounds and to obtain relevant information, Gangolli (157 to 166) proposed research into the inhibiting effect of ascorbic acid. In the chemistry of formation of N-nitroso compounds, Challis (16 to 55) describes the action of other inhibitors such as ammonia, primary amines, hydrazine, urea, sulphamic acid and its salts, hydroxylamine, azides, sulphur dioxide and bisulphite ion, the phenols and antioxidants. The most effective over a wide pH range is ascorbic acid, used in experimental "in vivo" studies on rats.

An identical conflictive situation occurs when ingesting, as active ingredient of a medicine, nitrosable drugs presenting a risk of carcinogenicity. Thus, Elder et al. (Lancet, 1, 1005–6, 1979, Lancet 2, 245, 1979) and Reed et al. (Lancet 1, 1234–5, 1979) related the appearance of a gastric carcinoma with treatment with cimetidine, an histamine $H_2$-receptor antagonist. Later, Foster et al. (Cancer Letters, 9, 47–52, 1980) showed by nitrosation of the abovementioned drug that the main reaction product is nitrosocimetidine (NC), whose structure and activity would be compatible with that of the known gastric carcinogen, N-methyl-N'-nitro-N'-nitrosoguanidine (MNNG).

"In vivo" studies with rats, performed by Habs (141 to 156), show that eight days treatment with a dose of 500 mg/kg of NC induces no toxic effect, whereas an $LD_{50}$ of 80–100 mg/kg was determined for MNNG, the $LD_{50}$ of NC being 1800–1900 mg/kg. Furthermore, Brambilla et al. (J. Pharmacol. Exp. Ther. 221 (1), 222–7, 1982) obtained no evidence of desoxyribonucleic acid (DNA) damage in any of the groups treated with equimolecular amounts of cimetidine (250 mg/kg) and nitrite (80 mg/kg). Lijinsky and Reuber (Cancer Res. 44 (2), 447–9, 1984) experimenting with male and female rats treated with a 0.5 mM solution of NC and MNNG for two years, found no effect with NC, whereas with MNNG, 45% or more of the rats developed adenomas and adenocarcinomas with a few hemangiosarcomas and neurosarcomas in the glandular stomach. These authors suggested that although NC may be formed in the stomach, on the basis of their negative results, the risk of cancer would be very small.

Since the $H_2$-receptor antagonists are chemically nitrosatable structures, like cimetidine, we have now discovered that, in fact, under gastric juice conditions, N-nitroso derivatives are formed. These may be detected in ppm by thin layer chromatography, and by the Griess reaction. Griess reagent: Chemical Analysis Ed. P. J. Elving; J. D. Winefordner, I. M. Kolthoff; John Wiley 1978, Vol. 8, p. 216; Colorimetric Determination of Non-metals, Ed. D. F. Boltz; J. A. Howell: Nitrite by modified Griess method.

It has also been discovered that, in the aqueous $H_2$-receptor antagonist ascorbate solutions prepared "in situ", of the competing nitrosation or nitrite elimination reactions, the latter is the predominant or sole reaction. This behaviour has also been verified in samples of gastric juice. Thus, the risk of carcinogenicity is non-existent, warranting the preparation of the corresponding ascorbates and their use as a medicinal drug.

Processes have been disclosed for the formation of alkali and alkali earth metal salts of L-ascorbic acid. According to French Pat. No. 1.498.600, the method consists of concentrating the aqueous solution, by distillation under vacuum, at a temperature below 30° C. of the azeotrope constituted by water-methyl ethyl ketone-propylene oxide. French Pat. No. 1.510.505 is restricted to the formation of the potassium salt, by mixture of the respective ascorbic acid and potassium hydroxide methanolic solutions, under an inert $N_2$ atmosphere. U.S. Pat. No. 4,251,449 teaches a process wherein an aqueous ascorbic acid solution is reacted with calcium carbonate under an inert $CO_2$ atmosphere at a temperature of 60° C., giving a 12 to 14% content in oxidised form in the calcium salt.

The application of these techniques for the preparation of $H_2$-receptor antagonist ascorbates has not been successful. In the best of cases, a very viscous liquid was formed when using methanol. A viscous mass was also formed when using an aqueous solution. After a laborious treatment, both methods gave solids which could not be dried because of their tendency to form pastes and they also decomposed (caramel appearance) and oxidised.

The freeze-drying and spray-drying processes are very costly, do not give crystalline salts and leave an undesirable water content, facilitating alteration of the product, which may be observed in solutions exposed to the ambient air.

When equimolar proportions of ascorbic acid and the $H_2$-receptor antagonist are mixed, after an extended premixing and mixing process, the result is a solid in which the crystals of both products are observed under the microscope. The product also has the drawbacks of: (a) decomposition for a localised heat effect, due to the friction and breakage of the crystalline structure, (b) oxidation during the premixing and mixing processes, (c) the composition is hard to reproduce and (d) unbalanced mixtures which may alter the competitivity of the reactions with the nitrous acid, all of which would be incremented in an industrial scale process.

SUMMARY OF THE INVENTION

These and other drawbacks have been overcome with the process of the invention, which allows new compounds containing ascorbic acid salts, mainly the enolates thereof, to be prepared, by reaction with the organic bases constituted by the histamine $H_2$-receptor antagonists, represented by $R_3$, such as:

(a) N"-cyano-N'-methyl-N-2-(5-methyl-1H-imidazol-4-yl)methylthioethylguanidine (cimetidine).

(b) N-(2-(((5-((dimethylamino)methyl)-2-furanyl) methyl)thio)ethyl)N'-methyl-2-nitro-1,1-ethenediamine (ranitidine).

(c) N-sulphamoyl-3-((2-guanidinothiazol-4-yl) methylthio)propionamidine (famotidine).

(d) N-(3-(3-(1-piperidinylmethyl)phenoxy)propyl)-1,2,5-thiadiazol-3,4-diamino-1-oxide (CM.5 antagonist).

(e) 2-(((((5((dimethylamino)methyl)-2-furanyl) methyl)-thio)ethylamino)-5-(2-methyl-5-methylpyridin-5-yl)-4-oxo-3-(H)-pyrimidine (CM. 10 antagonist).

Hereinafter, these compounds will be cited by their trivial names given in brackets.

The invention provides at least the following advantages:

a. the nitrosatable organic bases of $H_2$-receptor antagonists, when combined with ascorbic acid, give the respective ascorbates, where the nitrosation is inhibited, the potential cancerogenic risk being eliminated, and b. the reaction between the ascorbic acid and the organic base is conducted in a heterogenous phase in an inert solvent, such as dichloromethane, with stirring at temperatures from room temperature to reflux, to give microcrystalline forms of the ascorbates.

The ascorbates produce colourless aqueous solutions at pH 5.0–6.5, with famotidine ascorbate being soluble in water at concentrations of 7% at room temperature. For medicinal purposes, these ascorbates may be mixed with other compatible active ingredients, such as ascorbic, isoascorbic or desoxyascorbic acid or derivatives thereof.

Therefore, the invention provides compounds having histamine $H_2$-receptor antagonist properties, without any potential risk of carcinogenic effects.

The Formula I compounds preferably comprise the structural fraction of ascorbic, isoascorbic and desoxyascorbic acids. In the case of Formula I, with $C_4$ and $C_5$ being chiral carbons, the four stereoisomers of the lactone in enolic form of the 3-ketohexuronic acid are shown. The absolute configuration known for these four stereoisomers and their corresponding trivial names are:

$C_4(R)C_5(S)$, 3-ketohexuronic acid; L-ascorbic acid
$C_4(S)C_5(R)$, 3-ketohexuronic acid; D-ascorbic acid
$C_4(R)C_5(R)$, 3-ketohexuronic acid; D-isoascorbic acid
$C_4(S)C_5(S)$, 3-ketohexuronic acid; L-isoascorbic acid Another trivial name for isoascorbic acid is erythorbic acid. L-ascorbic acid, also known as vitamin C, may be called 3-oxo-L-gulofuranelactone (enolic form). Compounds of Formula I may be systematically named as derivatives of 2-oxo-3,4-dihydroxy-5-(1,2-dihydroxyethyl)-2,5-dihydrofurane. The desoxyascorbic acids are also called the enolic form of 3-keto-6-desoxyhexuronic acid lactone, with the corresponding 6-desoxyisoascorbic acids thereof.

The $C_6$–$C_5$ substituted derivatives are (5,6-O-isopropylidene)-L-ascorbic acid, 5,6-diacetate-L-ascorbic acid, 6-octonoate-L-ascorbic acid and 6-phosphate-L-ascorbic acid, for example.

The organic bases represented in Formula I by $R_3$ are characterised by forming a group of chemically nitrosatable compounds which, therefore, may present a risk of carcinogenicity, on forming N-nitroso derivatives.

More particularly, they form a group of labile N-nitroso derivatives.

The compounds represented by $R_3$ may have one or more basic functional groups, therefore when $Y=1$ in Formula I, X may be 1, 2 or 3, preferably, i.e. one mole of $R_3$ may take one, two or three moles of ascorbate to form a Formula I compound.

The Formula I compounds may be mono-, di- or triascorbates. They may also be formed by a composition having one equivalent of the Formula I ascorbate with one or two equivalents of ascorbic acid. The preferred acid is L-ascorbic acid.

Chemically, the Formula I compounds are organic salts of the enolic form of the respective 3-ketohexuronic acid lactones, now disclosed for the first time, and given the above cited trivial names, as ascorbic acid salts.

The Formula I compounds, i.e. L-ascorbic acid salts and the organic base represented by $R_3$, are formed by reacting both components, using an inert solvent as medium.

The inert solvents may be arranged in the following groups:

Alcohols: the low molecular weight alcohols such as methanol, propanol and iospropanol have proved to be inoperative.

Ketones: acetone has proved to be ineffective. Mixtures of the above solvents with dichloromethane have produced poor results.

Ethers: in general are harmful, the moreso the easier they form peroxides, such as 1,4-dioxane and tetrahydrofuran. Tert-butyl methyl ether may be used.

The high boiling point solvents are not appropriate either, because they are hard to remove. Among the halogenated solvents, although 1,2-dichloromethane, trichloroethylene, chloroform, carbon tetrachloride and 1,2-tetrachlorethane may be used, the preferred one is dichloromethane.

It is surprising that out of the large number of solvents, including the nitriles such as acetonitrile, the amides such as N-dimethylacetamide, N-dimethylformamide and hydrocarbons such as benzene, toluene, xylenes and their derivatives, chlorobenzene, nitrobenzene, etc., only dichloromethane has proved to be exceptional for the reaction. This, furthermore, is conducted in a heterogenous phase between the ascorbic acid and the organic base and provides the desired product in all cases, with a practically quantitative yield.

Regular analysis has confirmed the relative stability, deemed to be excellent, by titration of the ascorbic acid content with 2,6-dichlorophenol-indophenol. Specimens contacted with the ambient environment for thirty days have not shown oxidation. Rantitidine diascorbate has proved to be stable versus the monoascorbate which has to be preserved from light and air.

Japanese patent application No. 201934/1981 discloses a process for preparing famotidine salts in an aqueous medium, derived from aspartic and glutamic amino acids, to be used as stable compositions for intramuscular injection. The present invention provides more stable compositions of higher concentration, for use as injections, and with the advantage of the easy preparation represented by the formation of famotidine ascorbate, which is soluble up to 7% and at pH 5.6.

As indicated above, both ascorbic acid and the salts thereof, particularly the alkali and alkali earth salts, are poorly stable and may even be sufficiently instable as to cause alteration or decomposition, giving pasty, coloured mixtures, even with a caramel odour. Factors in this process are the temperature, moisture, atmospheric oxygen and pH of the compound whose salt it is wanted to obtain, particularly in the case of the ascorbyl-enolates.

An important objective of the process is to eliminate these drawbacks, which is achieved when a saturated fatty acid is included in the reaction medium in the ascorbate preparation process. The formation of $H_2$-receptor antagonist ascorbates also comprises the salts of such antagonists. Thus, stabilised products having excellent physiological properties and absence of mutagenic and hepatotoxic effects are obtained.

Thus, the process consists of the preparation, for example, of a famotidine ascorbyl-aspartate, instead of a famotidine ascorbyl ascorbate, i.e., the diascorbate.

Appropriate products for the purposes of the invention are the $H_2$-receptor antagonists, such as cimetidine, ranitidine, famotidine and others mentioned above. The salts of interest may be obtained with aspartic or glutamic acid, the enantiomers or racemes thereof and caffeic, ferulic and gallic acids. One interesting feature of these acids is their proven capacity to destroy nitrous acid.

The process comprises reacting a suspension of the $H_2$-receptor antagonist, in dichloromethane, first with one equivalent of one of the above mentioned acids, e.g. aspartic acid and thereafter with another equivalent of ascorbic acid. The reaction is conducted preferably at room temperature.

One process of choice for the preparation of the $H_2$-receptor antagonist ascorbates is first to prepare the salts thereof such as the monoascorbate, monoaspartate, monoglutamate, monocaffeate, monoferulate or monogallate, which are then isolated by filtration. They are then resuspended in dichloromethane and are then reacted with another equivalent of ascorbic acid to form the respective ascorbates listed below:

1. Cimetidine ascorbyl aspartate.
2. Ranitidine ascorbyl aspartate.
3. Famotidine ascorbyl aspartate.
4. Cimetidine ascorbyl glutamate.
5. Ranitidine ascorbyl glutamate.
6. Famotidine ascorbyl glutamate.
7, Cimetidine ascorbyl caffeate.
8. Ranitidine ascorbyl caffeate.
9. Famotidine ascorbyl caffeate.
10. Cimetidine ascorbyl ferulate.
11. Ranitidine ascorbyl ferulate.
12. Famotidine ascorbyl ferulate.
13. Cimetidine ascorbyl gallate.
14. $H_2$-receptor antagonist ascorbyl aspartate, ascorbyl glutamate, ascorbyl caffeate, ascorbyl ferulate and ascorbyl gallate.

Consequently, in the compounds represented by Formula I, $R_3$ also represents the said $H_2$-receptor antagonist salts where (X) is one and (Y) is preferably one molecular equivalent, from the above mentioned carboxylic acids and the $H_2$-receptor antagonist.

For the purpose of the invention, the reaction of the components is conducted preferably in dichloromethane, in the presence of a saturated fatty acid or mixtures thereof including acids having from 8 to 18 carbon atoms. Appropriate fatty acids are octanoic, 2-ethylhexanoic, lauric, palmitic, stearic acids and others, or mixtures thereof. The fatty acid moiety may be present in the reaction mixture from the outset or it may be added at the end. In either case, the amount may be from 5% to 200% by weight of the ascorbate being prepared.

The relative instability of both the $H_2$-receptor antagonists themselves and of their known salts is known. The compounds prepared according to the invention have proved to be extraordinarily stable to environmental factors.

$H_2$-receptor antagonist derived nitroso compounds were prepared according to the method proposed by Foster et al. (Cancer Letters, 9, 47–52, 1980) for cimetidine, under gastric juice and simulated gastric juice conditions. This first group of experiments comprises forming nitrosamines and, although the isolation yields are different in each case, they show that all these organic base structures are nitrosatable. A second run of experiments enabled it to be shown that those organic bases give rise to labile nitroso compounds.

When using $H_2$-receptor antagonist ascorbates, the nitrous acid is eliminated by reaction with the ascorbic acid in competition with the formation of nitrosamines. The action mechanisms of the ascorbates prove the absence of any potential cancerogenic risk for those compounds.

In accordance with Foster's process, when nitrosating 750 mg of cimetidine, about 100 mg of nitroso compound are isolated, in the form of an oil, containing nitrosocimetidine as main component. Thin layer chromatography (TLC) was performed on this raw reaction product, dissolved in 20 ml of acetone and stored at 5° C., using aluminium-silica gel chromatofoils (60 $F_{254}$ Merck) and chloroform-isopropanol (7:3) as eluant. $R_f$ was found to be 0.25. When acetone-water (9:1) was used, the difference over the starting product, cimetidine in the mixture, improved considerably, $R_f=0.65$ being found. Both values correspond to the nitroso derivative at $R_f=0.27$ found by Foster et al. when using chloroform-methanol (9:1) as eluant.

The amount of $H_2$-receptor antagonist ascorbate dissolved in gastric juice or simulated gastric juice did not exceed the permissible amount for the stomach "in vivo". Both media, preferably the latter, were used in "in vitro" tests, the latter constituting, according to Ziebarth (Archiv für Geschwulstforschung, 52 (6), 429–442, 1982), an experimental model providing concordant results. The nitrite concentration used for the tests of this invention is slightly higher than the one proposed by the above worker and should be considered to be abnormally high, considering that, according to Shank's results (207), with the ingestion at one time of 100 mg to 2300 mg of nitrates, 20 ppm to 500 ppm of nitrite are to be expected in the saliva, at a salivary flowrate of 50 ml/hour, and 8 mg of sodium nitrite, an amount much lower than that used in the tests themselves, would be found in the stomach.

Bunton et al (Helv. Chim. Acta, 43, 320–333, 1960) established the nitrous acid elimination rate equation in terms of the concentration of ascorbic acid and diazotable amines (o-chloroaniline, p-nitroaniline) and found that the value of the specific rate constant is 2.5 times greater in the diazotisation reaction. These results show that in an equimolecular mixture of ascorbic acid and organic base, by analogy, a large amount of nitroso derivative should be expected in the nitrosation.

Eizember et al. (J. Org. Chem., 44(5), 784–786, 1979, when discussing the relative destruction of the nitrosoamines, show that both 10% hydrochloric acid and asorbic acid are innefective for denitrosation at 70° C. for 20 and 180 minutes respectively. Thus it may be predicted that the nitrosocimetidine (NC) or the nitroso compound derivatives (NCD) which would be formed in a competition reaction, will not be destroyed by those reactants.

Surprisingly, contrarily to the results that might have been expected from the previous work (Bunton et al.; Eizember et al; vide supra), it has been discovered 1) that NC or NCD are labile nitroso compounds in aqueous media at acid pH; 2) with cimetidine ascorbates, the nitrous acid elimination reaction of the ascorbic acid is predominant in its competition with the nitrosation reaction; and 3) the formation of NC or NCD is outside the potential toxicity limits.

To this end, there was used the Griess reagent, adjusted to the technique of the experiment, to be able to quantify the denitrosation process and determine the amount of NCD. Thus, 0.02 ml of an NCD acetone solution was added to 20 ml of 1N hydrochloric acid containing sulphanilic acid (60 mg) and was incubated at 37° C. 0.4 ml samples were taken at intervals up to 90 minutes and were adjusted with water, sodium acetate and alpha-naphthylamine hydrochloride in a 25 ml graduated flask. The depth of colour was measured in a spectrophotometer at 520 nm. These results were confirmed by TLC by absence of spot at $R_f=0.25$ and $R_f=0.65$ for each eluant.

The position of the NCD spot in TLC was determined by touch reaction with the Griess reagent against a blank. The test was negative in the case of NC or NCD destruction.

The evolution of the possible nitroso compound was established applying the Griess test to saliva samples from children, men and women. In the absence of infection, values varying between 1.0 to 3.0 ppm in adolescents and young people and 10 ppm of nitroso ion in adults and old-aged persons, were found, in fasting. Without taking into account the rise in nitrite levels in case of ingestion of nitrate containing foods and considering a salivary flow over two hours, the stomach could contain from 0.24 to 1.2 mg nitrites, which means a maximum foreseeable amount of nitrosocimetidine of 0.26 mg (3.5 ppm), in accordance with the nitrosation under experimental conditions with simulated gastric juice.

For doses of 400 mg cimetidine and 36.4 mg of sodium nitrite in 75 ml of gastric juice at pH 1.5, with incubation at 37° C. for 60 minutes, 100 ppm of NCD were determined. The competing reactions of NC formation and nitrous acid destruction by the ascorbic acid was evaluated with cimetidine ascorbates at pH 1.0–3.5. 0.18 ppm of NC were found in 75 ml of artificial or simulated gastric juice, incubated at 37° C. with cimetidine ascorbate-nitrite (6:1 molar ratio; 679 mg and 18.2 mg respectively). With diascorbate and a 6:1 ratio, 0.13 ppm of NC were determined. The sensitivity of the method allows 0.05 ppm to be quantified.

Under the nitrosation conditions described by Foster et al. ranitidine in gastric juice causes the formation of nitroso derivatives and nitrosated degradation products, with $R_f=0.83$ (majority) and $R_f=0.55$ and 0.48 (minority). 770 mg of nitroso compounds, chromatographed with acetone-water eluant (9:1) were isolated in form of an oil from 940 mg of ranitidine.

Under gastric juice conditions at pH 1.5, 318 mg of ranitidine diascorbate and 18.2 mg sodium nitrite, after 60 minutes incubation, the spot at $R_f=0.83$ did not appear and when the triascorbate plus one equivalent of ascorbic acid was used, the spots at $R_f=0.55$ and 0.48 did not appear either. The spots at $R_f=0.83$ and 0.55 did not appear when incubating in 1N HCl plus sulphanilic acid, showing that they are labile nitroso derivatives or degradation products of ranitidine. Equivalent amounts of cimetidine ascorbate and diascorbate have brought males aged 55–60 years with duodenal ulcer diagnosis back to normal within the usual periods of cimetidine medication. Relapses and improvement maintainance cases were treated for one year continuously and for two years with breaks, at maintainance doses of 680 mg cimetidine ascorbate or 860 mg cimetidine diascorbate, normality being achieved.

The Griess test on "in vivo" nitrites in saliva (2 ml) controls in both men and women, with 200 mg ascorbate, was negative in all cases.

These results are complemented with the "in vivo" experiments of Habs, Brambilla and Lijinsky cited in the literature commented herein. In accordance with the invention, surprising structural lability of NC or NCD is observed and with the unexpected competitivity of ascorbic acid, it has been possible to establish as unmistakeable results that both the cimetidine ascorbates and the $H_2$-receptor antagonist ascorbates do not offer any potential carcinogenic risk, in spite of the fact that their organic bases, when nitrosated, give labile nitroso compounds.

The chemical mechanisms of the new inorganic base ascorbates, whereby any remote risk of their being gastric cancer inductors is removed, have been shown in "in vitro" and in "in vivo" tests.

The following has also been proven in cases of hyperchlorhydria:

(1) 0.08 ppm of NC is produced with cimetidine diascorbate at abnormally high nitrite concentrations. This limit is very much lower than would result from the nitrites from the saliva only and their combination with potentially carcinogenic secondary amines to be found in the environment and foodstuffs.

(2) the existence of an NCD$\rightleftarrows$H$_2$-receptor antagonist+HNO$_2$ equilibrium which, in the presence of nitrous acid trapping agents, such as sulphanilic acid, forming p-diazobenzene sulfonic acid (with alpha-naphthylamine, Griess reaction), or such as ascorbic acid, forming the diketo derivative (dihydroascorbic acid), is continuously displaced in the denitrosation direction.

(3) with the H$_2$-receptor antagonist ascorbates, theere is avoided the formation of nitroso compounds derived from possible degradation products, resulting from the nitrosation reaction.

Structurally, ranitidine and the H$_2$-receptor antagonist CM.10 are potential precursors of N-nitroso dimethylamine, a potent carcinogen. Furthermore, the latter is readily nitrosated into the pyrimidinone fraction to give nitrosamide. The H$_2$-receptor antagonist CM.5 is also a structural precursor of N-nitrosopiperidine. Famotidine, having various nitrosatable groups, namely sulphamide, guanidine and amidine is particularly reactive. All of this is confirmed by the formation of nitroso compounds and nitrosated degradation products.

For the purposes of the study described herein, it was assumed that the gastric juice nitrite content in fasting is low and would probably come from swallowed saliva, as per Schlag et al. (Lancet I, 727–729, 1980). During the first 60 minutes after the ingestion of food, during the digestion, the whole content of the stomach is impregnated with the gastric juice, becoming a homogenous acid mass, the chyme, having a volume of about 500 ml, according to Hunt and Spurell (J. Physiol. 113, 157–168, 1951). Under these circumstances, the resulting concentration of active substance is lower, although the amount of nitrite is very high relative to the saliva secretion, and warrants the amount preferably used, close to the 22.1 mg described by Walters et al. (Lyon: IARC Scientific Publ. No. 14, 181–192, 1976).

BRIEF DESCRIPTION OF THE DRAWINGS

In some of the Examples given below, reference is made to the following figures, wherein the transmission percentage is given on ordinates and the wave number (cm$^{-1}$) and the wave length in $\mu$m are given in abscissae.

EXAMPLES

EXAMPLE 1

Cimetidine L-ascorbate, in dichloromethane

Figure 1:
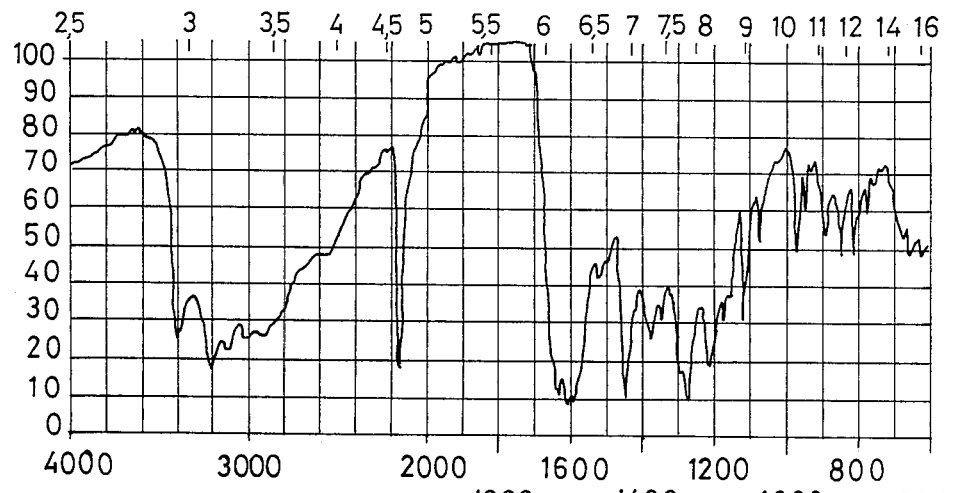
FIG. 1 is the infra red spectrum of cimetidine caffeate.

A mixture of 2.52 g (1 cmole) of cimetidine and 1.76 g (1 cmole) of ascorbic acid was suspended in 10 ml of dichloromethane. The suspension was heated to reflux and stirred for 3 hours, followed by filtering and washing with dichloromethane. Dry weight=4.29 g. Quantitative yield. M.p.: 124°–9° C., leaving traces that melt at 139° C. Stereoscopically homogenous white solid with crystalline concretions; soluble in water (pH 4.5). The infra red spectrum shows the characteristic lines corresponding to the ascorbate ion at 3500, 3395 and 1750 cm$^{-1}$.

Elementary analysis: Calculated: C: 44.85%, H: 5.64%, Found: C: 44.87%, H: 5.65%.

$[\alpha]_D^{20}=+45.4°$ (H$_2$O, 2%); +34.5° (CH$_3$OH, 2%).

Ascorbic acid: Calculated 41.1%; found: 41.2%.

EXAMPLE 2

Cimetidine L-ascorbate, in dichloromethane

A mixture of 2.52 g (1 cmole) of cimetidine and 1.76 g (1 cmole) of ascorbic acid was suspended in 10 ml of dichloromethane. The suspension was refluxed and stirred for 30 minutes, followed by filtering and washing with dichloromethane. Dry weight=4.24 g (Yield=99%). White solid. m.p. 128°–142° C.

EXAMPLE 3

Cimetidine L-ascorbate, in ispropanol 2.52 g (1 cmole) of cimetidine were suspended in 30 ml of isopropanol and 1.76 g (1 cmole) of ascorbic acid and traces of DBU (0.2 ml) were added. The suspension was stirred for 2.5 hours at room temperature. 20 ml of n-hexane were added to the suspension, followed by filtration, washing with n-hexane and the remains of solvent were removed by drying at reduced pressure. The solid obtained tended to form pasty clumps with time and it was not possible to isolate the ascorbate in a manageable solid form.

EXAMPLE 4

Cimetidine L-ascorbate, in dichloromethane

A mixture of 2.52 g (1 cmole) of cimetidine and 1.76 g (1 cmole) of ascorbic acid were suspended in 10 ml of dichloromethane. The suspension was stirred at room temperature for 60 minutes, followed by filtration and washing with dichloromethane. Dry weight=4.23 g. A bitter white solid which melts in various stages. Partial salt formation.

EXAMPLE 5

Cimetidine L-ascorbate, in isopropanol

Traces of DBU (0.2 ml) were added to a mixture of 2.52 g (1 cmole) of cimetidine and 1.76 g (1 cmole) of ascorbic acid in 30 ml of isopropanol. The suspension was heated to 35°-40° C. and held at that temperature with stirring for 60 minutes. A change of appearance of the white solid suspended in the isopropanol was observed. The mass was filtered and washed with isopropanol and, on attempting to dry it, a marked tendency to form a paste with a chewing gum appearance was observed. It was not possible to isolate the product in solid crystalline form.

EXAMPLE 6

Cimetidine L-ascorbate, in isopropanol

A mixture of 5.04 g (2 cmoles) of cimetidine and 3.52 g (2 cmoles) of ascorbic acid in 30 ml of isopropanol was heated to reflux. Complete solution was obtained after 15 minutes followed by immediate precipitation of a solid having a chewing gum appearance, which solidified with time. A further 20 ml of isopropanol were added. The product was filtered, but during filtration the product reassumed a pasty consistency, making its isolation impossible.

EXAMPLE 7

Cimetidine L-ascorbate, in methanol 2.52 g (1 cmole) of cimetidine were suspended in 10 ml of methanol and heated to 40° C., providing a complete solution. 1.76 g (1 cmole) of ascorbic acid was added. 40 ml of dichloromethane were added to the solution and a pasty looking solid was formed. It was decanted and thereafter soaked and broken down in isopropanol; the previous paste took on a powdery form. It was decanted and dried in a muffle at 60° C., giving a caramel coloured and looking mass, having undergone partial decomposition.

EXAMPLE 8

Ranitidine L-ascorbate, in dichloromethane

A mixture of 3.14 g (1 cmole) of ranitidine and 1.76 g (1 cmole) of ascorbic acid was suspended in dichloromethane (15 ml). The suspension was refluxed under stirring for 1.5 hours, followed by filtration, washing with dichloromethane and drying. Weight=4.8 g (Yield=98%). A stereoscopically homogenous slightly yellowish white solid with crystalline concretions was obtained; soluble in water (pH 3.5). M.P.: 117°-127° C. Characteristic in the infra red spectrum are the lines corresponding to the ascorbate ion at 3500, 3395 and 1750 cm$^{-1}$.

Elementary analysis: Calculated: C: 46.52%, H: 6.57%; Found: C: 46.50%, H: 6.55%. Ascorbic acid: Calculated: 35.9%; Found: 35.4%, $[\alpha]_D^{20} = +10.1°$ (2%, H$_2$O), $+18.2°$ (2%, MeOH).

The product has to be preserved from the air and light.

EXAMPLE 9

Ranitidine L-ascorbate, in dichlormethanol

A mixture of 3.14 g (1 cmole) of ranitidine and 1.76 g (1 cmole) of ascorbic acid was suspended in dichloromethane (15 ml) and was refluxed for 3 hours, following by filtering, washing with dichloromethane and drying. Weight=4.8 g (yield 98%). The characteristics of the product obtained were identical to those of the previous Example.

EXAMPLE 10

Ranitidine L-ascorbate, in isopropanol

A mixture of 3.14 g (1 cmole) of ranitidine and 1.76 g (1 cmole) of ascorbic acid was suspended in isopropanol (15 ml) and stirred at room temperature for 60 minutes, followed by filtration and washing with dichloromethane and drying. Weight=4.58 g (yield 93.5%). A stereoscopically homogenous slightly yellowish white product with crystalline concretions was obtained. M.P.: softening at 95° C., almost complete melting at 109°-120° C. and complete and 135° C.

EXAMPLE 11

Ranitidine L-ascorbate, in acetone

A mixture of 3.14 g (1 cmole) of ranitidine and 1.76 g (1 cmole) of ascorbic acid was suspended in 15 ml of acetone and stirred at room temperature for 1.5 hours, followed by filtration and washing with acetone, giving a solid which lumped during drying.

The experiment was repeated with heating to reflux: after 10 minutes refluxing, a solid pasty block which could not be isolated in solid form was formed.

EXAMPLE 12

Famotidine L-ascorbate, in dichloromethane

A mixture of 0.5 g (0.15 cmole) of famotidine and 0.26 g (0.15 cmole) of ascorbic acid was suspended in dichlormethane (5 ml). The suspension was refluxed for 60 minutes, followed by filtration, washing in dichlormethane and drying. Weight=0.75 g (yield 99%). A white solid, showing the formation of acicular crystals under stereoscopic examination. M.p.: 141°-5° C. (d). Characteristic in the infra red spectrum are the ascorbate ion lines at 3500, 3395 and 1750 cm$^{-1}$.

Elementary analysis: Calculated: C: 32.75%, H: 4.51%; Found: C: 32.76%; H: 4.51%.

$[\alpha]_D^{20} = +37.6°$ (H$_2$O, 2%). Solubility in water: 7.5% (pH=5.9).

Ascorbic acid: Calculated: 34.3%, Found: 34.2%.

The product has to be preserved from the air and light.

EXAMPLE 13

Famotidine L-ascorbate, in dichloromethane

A mixture of 0.5 g (0.15 cmole) of famotidine and 0.26 g (0.15 cmole) of ascorbic acid was suspended in dichloromethane (5 ml) and was refluxed for 2 hours, followed by filtration, washing with dichlormethane and drying. Weight 0.75 g (yield: 99%). A white solid, showing the formation of acicular microprisms of identical characteristics to those of the previous Example under stereoscopic examination.

EXAMPLE 14

CM.5 antagonist L-ascorbate

Following Example 1 and replacing the cimetidine by the equivalent amount of N-(3-(3-(1-piperidinylmethyl)-phenoxy)propyl)-1,2,5-thiadiazole-3,4-diamine-1-oxide (3.63 g; 1 cmole), the compound of the title was obtained, with an almost quantitative yield. It is water soluble. Characteristic in the infra red spectrum are the lines corresponding to the ascorbate ion at 3500, 3395 and 1750 cm$^{-1}$.

Ascorbic acid: Calculated 32.6%; Found 31.5%.

The water soluble diascorbate was obtained using two equivalents of ascorbic acid. Stereoscopic examination revealed the formation of microcrystalline concretions. The product has to be preserved from the air and light.

EXAMPLE 15

CM.10 antagonist L-ascorbate

Following Example 1 and replacing the cimetidine with the equivalent amount of 2-((((5-((dimethylamino)-methyl)-2-furanyl)methyl)thio)-ethylamino)-5-(2-methyl-5-pyridinmethyl-5-yl)-4-oxo-(3H)pyrimidine (4.13 g; 1 cmole), the compound of the title was obtained with practically a quantitative yield. It is water soluble. Characteristic in the infra red spectrum are the lines corresponding to the ascorbate ion at 3500, 3395 and 1750 cm$^{-1}$. Stereoscopic examination revealed the formation of microcrystalline concretions.

Ascorbic acid: Calculated: 29.9%; Found: 28.9%.

EXAMPLE 16

Cimetidine diascorbate

A mixture of 2.52 g (1 cmole) of cimetidine and 3.52 g (2 cmole) of ascorbic acid was suspended in 10 ml of dichloromethane, was refluxed and stirred for 3 hours, followed by filtration and washing with dichloromethane. Dry weight=5.97 g (yield=99%). M.p.: 130°-5° C. (d)

$[\alpha]_D^{20} = +13.3°$ (H$_2$O, 2%); +25.4° (CH$_3$OH, 2%).

Ascorbic acid: calculated 58.2%; Found: 58%.

The product has to be preserved from the air and light.

EXAMPLE 17

Famotidine diascorbate

A mixture of 87.8 mg (0.26 mmole) of famotidine and 91.6 mg (0.52 mmole) of ascorbic acid were suspended in dichloromethane (5 ml) and was refluxed for 3 hours, followed by filtration, washing with dichloromethane and drying. Weight=174 mg. Quantitative yield. M.P.=113°-9° C.

$[\alpha]_D^{20} = +33.5°$ (H$_2$O, 1.2%).

Ascorbic acid: Calculated 51.1%. Found 50.9%.

The product has to be preserved from the air and light.

EXAMPLE 18

Ranitidine diascorbate

A mixture of 3.14 g (1 cmole) of ranitidine and 3.52 g (2 cmole) of ascorbic acid was suspended in dichloromethane (15 ml), was heated to reflux and stirred for 3 hours under reflux, followed by filtration, washing with dichloromethane and drying. Weight=6.35 g (yield=95.3%). A slightly yellowish white solid. M.p.: 96°-110° C. one part and 125°-35° the remainder (d).

$[\alpha]_D^{20} = +39.5°$ (H$_2$O, 2%); +43.2° (CH$_3$OH, 2%).

Ascorbic acid: Calculated: 52.8%. Found: 52.2%.

The product has to be preserved from the air and light.

EXAMPLE 19

Cimetidine 0-5,6-diacetyl-L-ascorbate

Following the process of Example 1 and using 1 cmole of 5,6-diacetate-L-ascorbic acid and 1 cmole of cimetidine, the compound of the title was obtained after 6 hours at room temperature. Quantitative yield. The product has to be preserved from the air and light.

EXAMPLE 20

Cimetidine 5,6-0-(1-methylethylidene)-L-ascorbate

Following the process of Example 1 and using 1 cmole of 5,6-0-(1-methylethylidene) acid and 1 cmole of cimetidine, the compound of the title was obtained after 6 hours at room temperature. Quantitative yield. The product has to be preserved from the air and light.

EXAMPLE 21

Rantidine 6-phosphate-L-ascorbate

Following the process of Example 8 and using 1 cmole of 6-phosphate-L-ascorbic acid and 1 cmole of ranitidine, the compound of the title was obtained after 2 hours at room temperature. Quantitative yield. The product has to be preserved from the air and light.

EXAMPLE 22

Ranitidine diascorbate

A mixture of 3.14 g (1 cmole) of ranitidine and 3.52 g (2 cmole) of ascorbic acid was suspended in dichloromethane (20 ml) with stirring for 5 hours at room temperature (25°-28° C.), followed by filtration, washing with dichloromethane and drying. Weight=6.54 g (yield=98.2%). Slightly yellowish white solid. M.p. 95° C. solftening and melting at 110°-130° C.

EXAMPLE 23

Famotidine diascorbate

A mixture of 0.5 g (0.15 cmole) of famotidine and 0.52 g (0.3 cmole) of ascorbic acid was suspended in dichloromethane (10 ml). The mixture was stirred for 5 hours at room temperature, followed by filtration, washing with dichloromethane and drying. Quantitative yield. A diascorbate having characteristics identical to Example 17.

EXAMPLE 24

Ranitidine triascorbate

A mixture of 3.14 g (1 cmole) of ranitidine and 5.28 g (3 cmole) of ascorbic acid was suspended in dichloromethane (20 ml). It was stirred at room temperature for 5 hours, followed by filtering, washing with dichlormethane and drying. Yield=97.4%. M.p.: 115°-130° C. (d).

Ascorbic acid: Calculated 41.8%; Found 42%.

The product has to be preserved from the air and light.

EXAMPLE 25

(a) Cimetidine caffeate

A mixture of 1.26 g (0.5 cmole) cimetidine and 0.95 g (0.5 cmole) of caffeic acid (97%) were suspended in 12 ml of dichloromethane. The mixture was stirred for 2 hours at room temperature, followed by filtration and washing with dichloromethane. Dry weight: 2.17 g. Quantitative yield. M.p.: 126°-130° C. IR FIG. 1.

(b) Cimetidine ascorbyl caffeate

A mixture of 1.08 g (0.25 cmole) of cimetidine caffeate and 0.44 g (0.25 cmole) of ascorbic acid was suspended in dichloromethane (10 ml) and stirred for 2 hours at room temperature, followed by filtration, washing with dichloromethane and drying. Weight=1.51 g. Quantitative yield. A stereoscopically homogenous microcrystalline product having a mother-of-pearl gloss. M.p. 122°–126° C. It was suspended in a solution of lauric acid in dichloromethane, stirred, filtered and dried.

EXAMPLE 26

(a) Famotidine aspartate

Figure 2:
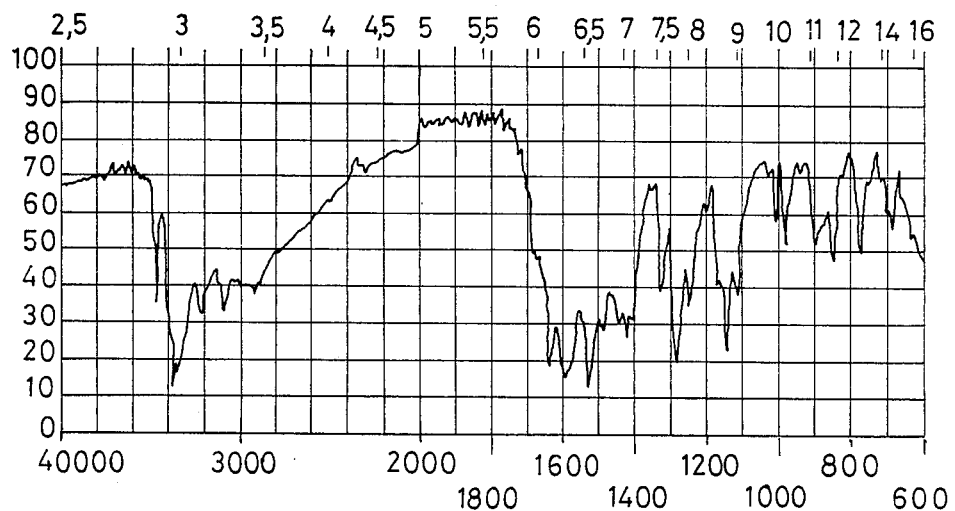
FIG. 2 is the infra red spectrum of famotidine aspartate.

A mixture of 0.56 g (0.166 cmole) of famotidine and 0.222 g (0.166 cmole) of aspartic acid was suspended in dichloromethane (10 ml). The mixture was stirred for 3 hours at room temperature, was filtered, washed with dichloromethane and dried. Weight: 0.782 g. Quantitative yield. Stereoscopically homogenous white microcrystalline solid, similar to milky quartz. Slightly bitter taste. M.P.: 165°–170° C. IR FIG. 2.

(b) Famotidine ascorbyl aspartate

A mixture of 0.35 g (0.07 cmole) of famotidine aspartate and 0.13 g (0.07 cmole) of ascorbic acid were suspended in 5 ml of dichloromethane and stirred for 2 hours at room temperature, followed by filtration, washing in dichloromethane and drying. Weight: 0.46 g. Yield 96%. The product was suspended in a solution of lauric acid in dichloromethane, stirred, washed and dried.

EXAMPLE 27

(a) Cimetidine aspartate

A mixture of 0.66 g (0.5 cmole) of aspartic acid and 1.26 g (0.5 cmole) of cimetidine was suspended in 15 ml of dichloromethane. It was stirred for 3 hours at room temperature, filtered, washed with dichloromethane and dried. Weight 1.87 g (yield 97.5%). A stereoscopically homogenous microcrystalline white solid. M.p.: 141°–142° C. In the infra red spectrum the lines at 3200, 3130, 2160, 1620 and 1585 cm$^{-1}$ are characteristic.

(b) Cimetidine ascorbyl aspartate

Figure 3:
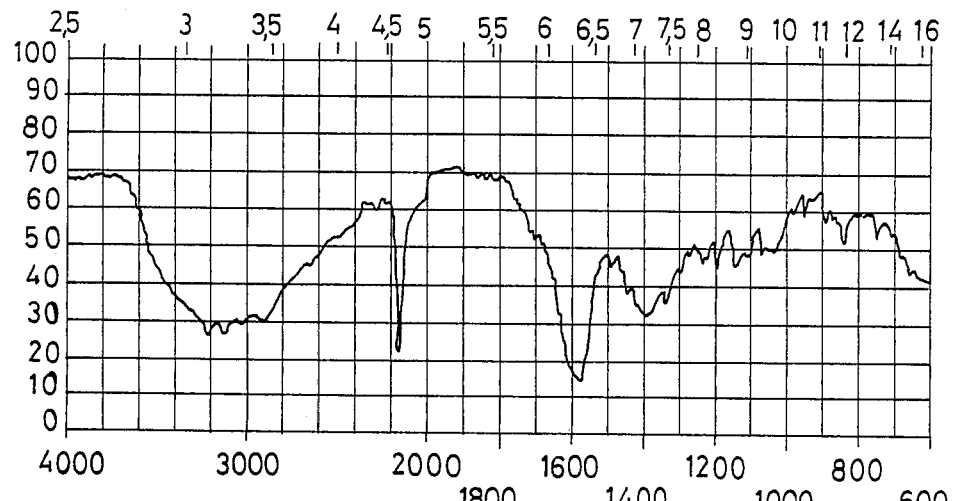
FIG. 3 is the infra red spectrum of cimetidine ascorbyl aspartate.

A mixture of 0.96 g (0.25 cmole) of cimetidine aspartate and 0.44 g (0.25 cmole) of ascorbic acid was suspended in 10 ml of dichloromethane. The mixture was stirred for 2 hours at room temperature, was filtered, washed with dichloromethane and dried. Weight 1.39 g (yield 99%). IR FIG. 3.

EXAMPLE 28

(a) Ranitidine aspartate

Figure 4:
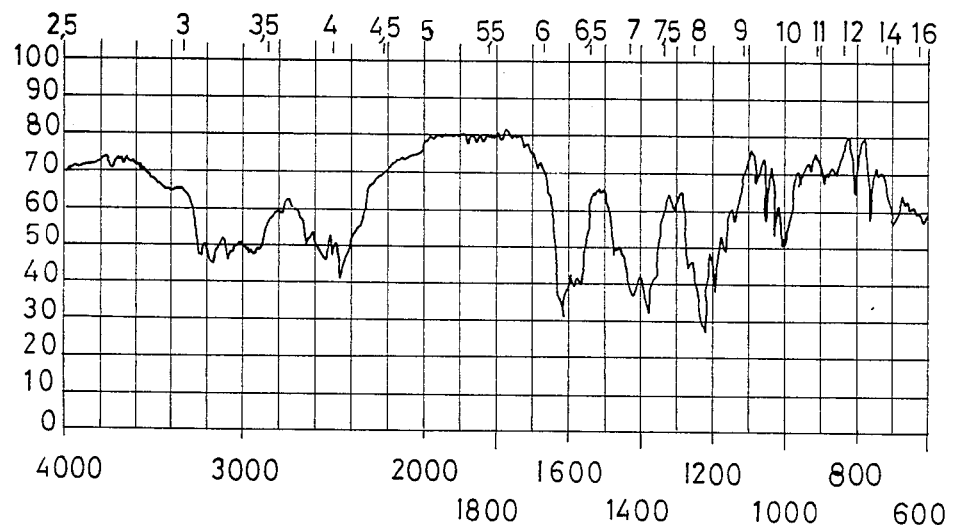
FIG. 4 is the infra red spectrum of ranitidine aspartate.

A mixture of 1.57 g (0.5 cmole) of ranitidine and 0.66 g (0.5 cmole) of aspartic acid was suspended in 15 ml of dichloromethane. The mixture was stirred for 3 hours at room temperature, was filtered, washed with dichloromethane and dried. Weight: 2.16 g (yield 97%). M.p. 163°–166° C. IR FIG. 4.

(b) Ranitidine ascorbyl aspartate

Figure 5:
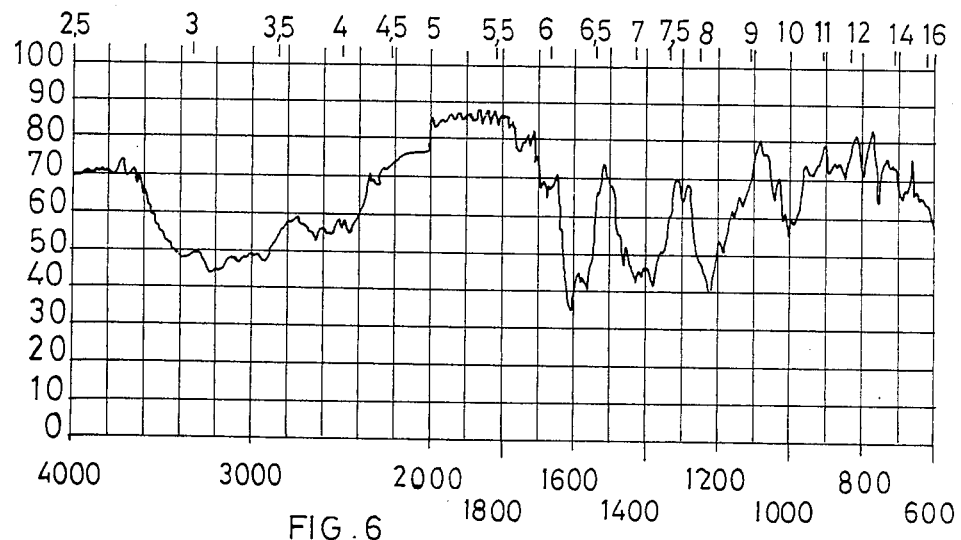
FIG. 5 is the infra red spectrum of ranitidine ascorbyl aspartate.

A mixture of 1.11 g (0.25 cmole) of ranitidine aspartate and 0.44 g (0.25 cmole) of ascorbic acid was suspended in dichloromethane (10 ml). The mixture was stirred for 2 hours at room temperature, was filtered, washed with dichloromethane and dried. Weight 1.52 g (yield 98%). IR FIG. 5.

EXAMPLE 29

Figure 6:
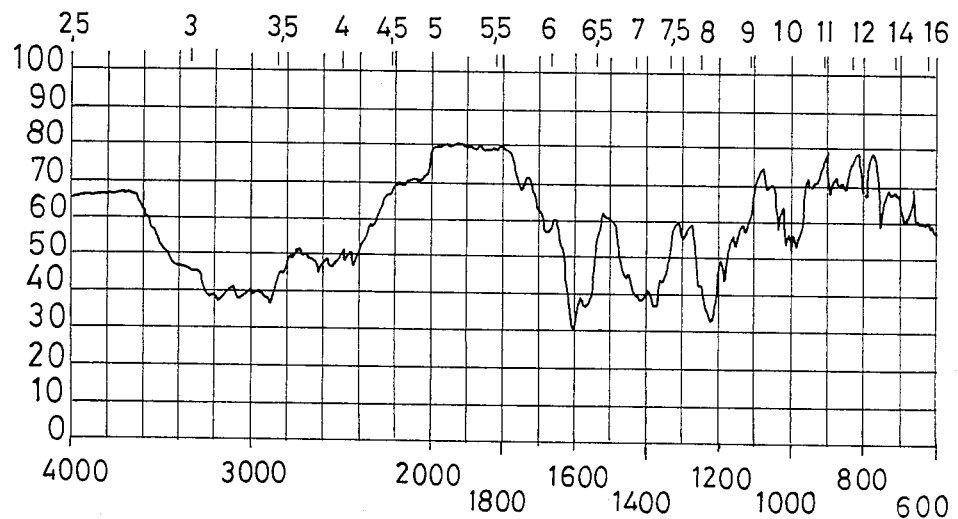
FIG. 6 is the infra red spectrum of ranitidine ascorbyl aspartate (palmitic acid).

Ranitidine ascorbyl aspartate 0.33 g (0.25 cmole) of aspartic acid, 0.785 g (0.25 cmole) of ranitidine and 0.45 g (0.25 cmole) of ascorbic acid were added to a solution of palmitic acid (1.115 g) in dichloromethane (10 ml). The mixture was stirred for 3 hours at room temperature, was filtered without washing and dried in a current of cold air. Weight 1.46 g. IR FIG. 6. A stereoscopically homogenous white solid, translucent microflakes. Is unaltered by ambient conditions.

EXAMPLE 30

Cimetidine ascorbyl aspartate 0.33 g (0.25 cmole) of aspartic acid, 0.63 g (0.25 cmole) of cimetidine and 0.45 g (0.25 cmole) of ascorbic acid were added to a solution of palmitic acid (0.96 g) in dichloromethane. The mixture was stirred for 3 hours at room temperature, was filtered without washing and dried in a current of cold air. (The liquors were recycled). Dry weight: 1.28 g. A stereoscopically homogenous white solid, translucent microflakes. Is unaltered by ambient conditions.

EXAMPLE 31

(a) Ranitidine caffeate

A mixture of 1.57 g (0.5 cmole) of ranitidine and 0.95 g (0.5 cmole) of caffeic acid were suspended in dichloromethane (15 ml). The mixture was stirred for 2 hours 30 minutes at room temperature, was filtered, washed with dichloromethane. Dry weight 2.4 g. Quantitative yield.

(b) Ranitidine ascorbyl caffeate

A mixture of 1.26 g (0.25 cmole) of ranitidine caffeate and 0.44 g (0.25 cmole) of ascorbic acid were suspended in 10 ml of dichloromethane. The mixture was stirred for 2 hours at room temperature, was filtered, washed with dichloromethane and dried. Weight: 1.67 g. Quantitative yield. The mixture was suspended in a solution of lauric acid in dichloromethane, stirred, filtered and dried.

EXAMPLE 32

Ranitidine ascorbate 2.45 g of palmitic acid were dissolved in 10 ml of dichloromethane. Thereafter, 0.88 g (0.5 cmole) of ascorbic acid and 1.57 g (0.5 cmole) of ranitidine were added. The mixture was stirred for 3 hours at room temperature, was filtered and washed with the same liquors. Dry weight: 3.56 g. This solid is unaltered by ambient conditions.

EXAMPLE 33

Cimetidine ascorbate 0.88 g (0.5 cmole) of ascorbic acid and 1.26 g (0.5 cmole) of cimetidine were added to a solution of stearic acid (2.14 g) in dichloromethane (q.s.). The mixture was filtered without washing and dried. Weight: 2.5 g. A stereoscopically homogenous white solid. Is unaltered by ambient conditions.

EXAMPLE 34

Ranitidine ascorbate

Following Example 32 and replacing the palmitic acid by the same amount of lauric acid, the compound of the title was obtained with a similar yield, being stereoscopically homogenous.

EXAMPLE 35

(a) Ranitidine ferrulate

A mixture of 1.57 g (0.5 cmole) of ranitidine and 0.97 g (0.5 cmole) of ferrulic acid were suspended in 15 ml of dichloromethane. The mixture was stirred at room temperature for 2 hours, was filtered and washed with dichloromethane. Dry weight: 2.5 g. Quantitative yield.

(b) Ranitidine ascorbyl ferrulate

A mixture of 1.54 g (0.5 cmole) of ranitidine ferrulate and 0.88 g (0.5 cmole) of ascorbic acid was suspended in 15 ml of dichloromethane. The mixture was stirred for two hours at room temperature, was filtered, washed with dichloromethane and dried. Weight 2.4 g. Quantitative yield. A stereoscopically homogenous, microcrystalline solid. Was suspended in a solution of palmitic acid in dichloromethane, stirred, filtered and dried.

EXAMPLE 36

Cimetidine ascorbyl ferrulate

Following Example 35 and replacing the ranitidine with an equivalent amount of cimetidine, the compound of the title was obtained with a similar yield and in stereoscopically homogenous form. It was suspended in a solution of palmitic acid in dichloromethane, stirred, filtered and dried.

EXAMPLE 37

Famotidine ascorbyl ferrulate

Following Example 35 and replacing the ranitidine with the equivalent amount of famotidine, the compound of the title was obtained with a similar yield and in stereoscopically homogenous form. Was suspended in a solution of stearic acid in dichloromethane, stirred, filtered and dried.

EXAMPLE 38

Cimetidine ascorbyl glutamate

Following Example 30 and replacing the aspartic acid with the equivalent amount of glutamic acid, the compound of the title was obtained with a similar yield and in stereoscopically homogenous microcrystalline form.

What we claim is:

1. A process for the preparation of $H_2$-receptor antagonist ascorbate compounds derived from the lactone form of 3-ketohexuronic acid of Formula I:

$$\left[ \begin{array}{c} R_1H_2C-R_2OHC \quad H \quad OH \\ \diagdown \\ O \\ \| \\ O \end{array} \right]_X \cdot (R_3)_Y \quad (I)$$

or the O-alkylidene,5,6-diacyl, 6-acyl derivatives thereof having two to sixteen carbon atoms, or a 6-phosphate, where X may be 1, 2 or 3 and Y may be 1 or 2, $R_1$ and $R_2$ are both hydrogen or $R_1$ may be hydroxyl, $R_2$ may be hydrogen $R_3$ being an organic base selected from N"-cyano-N'-methyl-n-2-(5-methyl-1H-imidazol-4-yl)methylthioethylguanidine (cimetidine), N-(2-(((5-((dimethylamino)methyl)-2-furanyl)methyl)-thio)ethyl)N'-methyl-2-nitro-1,1-ethenediamine (ranitidine), N-sulphamoyl-3-((2-guanidinothiazol-4-yl)methylthio)-propionamidine (famotidine), N-(3-(3-1-piperidinylmethyl)phenoxy)propyl)-1,2,5-thiadiazol-3,4-diamino-1-oxide (CM.5 antagonist), 2-(((5((dimethylamino)methyl)-2-furanyl)methyl)thi-o)ethylamino)-5-(2-methyl-5-methylpyridin-5-yl)-4-oxo-3-(H)pyrimidine (CM. 10 antagonist), or salts thereof which comprises, reacting a 3-ketohexuronic acid or a derivative thereof of the formula II $$R_1H_2C-R_2OHC \quad H \quad OH \atop \diagdown \atop O \quad OH \atop \| \atop O \quad (II)$$

where $R_1$ and $R_2$ are as hereinbefore defined, at a temperature of 0° C. to 60° C. in the presence of an inert solvent, with an organic base or a salt thereof represented by $R_3$ as hereinbefore defined, to give a compound of Formula I.

2. The process of claim 1, wherein the reaction is conducted in presence of a saturated fatty acid.

3. The process of claim 1 or 2, wherein the compound of Formula II is selected from the optically active isomers of ascorbic acid, isoascorbic acid, deoxyascorbic acid, 6-phosphate ascorbic acid, 5,6-diacetyl ascorbic acid, 6-octanoate ascorbic acid, O-methyl-ethylidene ascorbic acid.

4. The process of claim 1 or 2, wherein the salts of $R_3$ are the salts of aspartic acid, glutamic acid, the enantiomers or racemes thereof, caffeic acid, ferulic acid or gallic acid.

5. The process of claim 1, wherein the inert solvent is tertbutyl methyl ether, 1,2-dichloroethane, trichloroethylene, chloroform, carbon tetrachloride, 1,2-tetrachloroethane, ethyl acetate, isopropyl acetate or dichloromethane.

6. The process of claim 2, wherein said saturated fatty acid has from eight to eighteen carbon atoms.

7. The process of claim 6, wherein said fatty acid is selected from octanoic acid, 2-ethylhexanoic acid, lauric acid, palmitic acid, stearic acid and mixtures thereof.

8. The process of claim 1 or 2, wherein L-ascorbic acid and derivatives thereof are selected as Formula II compounds.

9. the process of claim 1, wherein the salts of the compounds represented by $R_3$ are obtained by reaction of, on the one hand, an $H_2$-receptor antagonist selected from:

N"-cyano-N'-methyl-N-2-(5-methyl-1H-imidazol-4-yl)methylthioethylguanidine (cimetidine), N-(2-(((5-((dimethylamino)methyl)-2-furanyl)methyl-thio)ethyl)N'-methyl-2-nitro-1,1-ethenediamine (ranitidine), N-sulphamoyl-3-((2-guanidinothiazol-4-yl)methylthio)-propionamidine (famotidine), N-(3-(3-(1-piperidinylmethyl)phenoxy)propyl)-1,2,5-thiadiazol-3,4-diamino-1-oxide (CM.5 antagonist), 2-((((5((dimethylamino)methyl)-2-furanyl)methyl)thi-o)ethylamino)-5-(2-methyl-5-methylpyridin-5-yl)-4-oxo-3-(H)pyrimidine (CM. 10 antagonist)

and, on the other hand, an acid selected from aspartic acid, glutamic acid, caffeic acid, ferulic acid or gallic acid.

10. The process of claim 9, wherein a suspension of the salts of the compound represented by $R_3$ are reacted with an equivalent of ascorbic acid or an ascorbic acid derivative.

* * * * *